US00PP20554P2

(12) United States Plant Patent
Utecht

(10) Patent No.: US PP20,554 P2
(45) Date of Patent: Dec. 15, 2009

(54) ***PELARGONIUM* PLANT NAMED 'FISDELAV'**

(50) Latin Name: *Pelargonium×hortorum*
Varietal Denomination: Fisdelav

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/291,090

(22) Filed: Nov. 6, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Annette H Para
(74) *Attorney, Agent, or Firm*—S. Matthew Edwards

(57) ABSTRACT

A new *Pelargonium* plant named 'Fisdelav,' particularly distinguished by the deep purple-pink flower with distinct red-purple eyes, medium sized inflorescences not too high above the foliage, mid season start of flowering, medium green foliage, relatively large leaves without zonation, and compact, low mounding habit, relatively small plants during cultivation, and medium size during the summer months.

1 Drawing Sheet

Latin Name of the genus and species of the plant claimed: *Pelargonium×hortorum.*

Varietal denomination: 'Fisdelav'.

BACKGROUND OF THE NEW PLANT

The present invention comprises a new zonal Geranium, botanically known as *Pelargonium×hortorum* and hereinafter referred to by the variety name 'Fisdelav.'

'Fisdelav' is a product of a planned breeding program. The new cultivar 'Fisdelav' has purple-pink flowers with large red eyes, medium green foliage without zonation, and about medium sized, low, mounding, bushy plant habit.

'Fisdelav' originated from a hybridization made in the summer 2004 in a controlled breeding program in Hillscheid, Germany. The female parent was the unpatented hybrid seedling designated 'K96-835-4,' with single type, lavender flowers, and grass green foliage without zonation, and relatively vigorous growth.

The male parent of 'Fisdelav' was the commercial variety 'Katinka,' (Plant Breeder's Rights protected 'Klegrato') having lavender, semi double flowers, with purple eyes, medium green leaves without zonation, and compact plant habit.

'Fisdelav' was selected as one flowering plant within the progeny of the stated cross in the spring of 2005 in a controlled environment in Galdar, Gran Canaria, Spain.

The first act of asexual reproduction of 'Fisdelav' was accomplished when vegetative cuttings were taken from the initial selection in the fall of 2005 in a controlled environment in Galdar, Gran Canaria, Spain.

Horticultural examination of plants grown from cuttings of the plant initiated in March of 2006 in Hillscheid, Germany, and continuing thereafter, has demonstrated that the combination of characteristics as herein disclosed for 'Fisdelav' are firmly fixed and are retained through successive generations of asexual reproduction.

'Fisdelav' has not been observed under all possible environmental conditions. The phenotype may vary significantly with variations in environment such as temperature, light intensity and day length.

Plant Breeders' Rights for this cultivar was applied for in Canada on Mar. 27, 2008 and in Germany on Mar. 25, 2007. 'Fisdelav' has not been made publicly available more than one year prior to the filing of this application.

DESCRIPTION OF THE DRAWING

The accompanying photographic drawing shows typical flower and foliage characteristics of 'Fisdelav' with colors being as true as possible with an illustration of this type. The photographic drawing shows a flowering potted plant, about three months old of the new variety. The photograph was taken on Apr. 27, 2007 in Hillscheid, Germany.

DETAILED BOTANICAL DESCRIPTION

The measurements were taken in Hillscheid, Germany, on Aug. 28, 2008 on about 6 months old plants growing in the outdoor trial field. Culture of these plants started in early March when rooted young plants were planted into 12 cm pots and were grown out, unpinched, on greenhouse benches. They were transplanted, 3 each, into tubs, diameter 31 cm, in mid May and were placed outdoors.

Color chart used: The Royal Horticultural Society Colour Chart (R.H.S.), 2001.

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* (common name zonal *Geranium*) as a new and distinct variety.

1. Deep purple-pink flowers with distinct red/purple-red 'eyes'
2. Relatively large inflorescences, and medium sized, semi double flowers
3. Grass green foliage, relatively large leaves without zonation 4. Fairly compact during spring time cultivation, later medium sized habit
5. Well branched, mounding habit with the flower heads not very high above the foliage.
6. Early spring flowering response
7. Suitable as a bedding plant and for larger containers

COMPARISON WITH COMMERCIAL CULTIVARS

TABLE 1

DIFFERENCES BETWEEN THE NEW VARIETY 'FISDELAV' AND SIMILAR VARIETIES

| | 'FISDELAV' | 'FISROHOT' (U.S. Plant Pat. No. 14,886) |
|---|---|---|
| Flower color, markings on petals | Purple-red eyes, upper and lower petals | No red eyes, upper petals with white bases |
| Length of peduncles | Short to medium | Long, high above the foliage |
| Leaf zonation | Absent | Distinct |
| Plant size | Medium | Tall |
| | 'FISDELAV' | 'FISRODEEP' (U.S. Ser. No. 12/228,729) |
| Flower color, markings on petals | Purple-red eyes, upper and lower petals | No red eyes, upper petals with white bases |
| Plant size in May 2008 | 11.7 cm in height<br>21.7 cm horizontal diameter | 16.0 cm in height<br>26.2 cm horizontal diameter |
| Leaf width | 9.5 cm | 10.5 cm |
| Flower diameter | 4.7 cm | 5.2 cm |
| | 'FISDELAV' | 'AMRI PUR' (Co-applied) |
| Flower markings | Red 'eyes' on upper and lower petals | Upper petals with scarlet bases |
| Main flower color | N74B | (Somewhat deeper) Between N66B and N74A |

Plant:

*Form, growth and habit.*—Medium vigor, bushy, well branched and mounding habit, medium sized.

*Plant height.*—11.7 cm in May, 17–20 cm in late August.

*Plant height (inflorescence included).*—26–29 cm in late August.

*Plant width.*—21.7 cm in May, 27–33 cm in late August.

Stem:

*Number of branches.*—8.5 in May.

*Color of stem.*—Light green, RHS 143C.

*Length of stem.*—Approximately 10–15 cm.

*Diameter.*—0.7–0.9 cm.

*Length of internodes.*—1.5–2.5 cm.

*Texture.*—Covered with dense, very short hair.

Foliage:

*Immature, leaf color, upper surface.*—RHS 143A.

*Lower surface.*—RHS 138A–138B.

*Mature, leaf color, upper surface.*—RHS 137D.

*Lower surface.*—RHS 138A.

*Length.*—6.5 cm.

*Width.*—9.5 cm.

*Shape.*—Kidney-shape (reniform), with relatively distinct lobes (for a *Pelargonium hortorum* variety), and with open base and palmate venation.

*Base shape.*—Cordate.

*Apex shape.*—Rounded.

*Margin.*—Bi-crenate.

*Texture.*—Velvety, both surfaces pubescent.

*Color of zone.*—Nearly no zonation, possibly a somewhat deeper green ring, RHS 147A.

*Color of veins, upper surface.*—RHS 144A, indistinct.

*Color of veins, lower surface.*—RHS 144B.

*Petiole, color.*—RHS 143C.

*Petiole, length.*—Approximately 7–10 cm (in August).

*Diameter of petiole.*—3 mm.

*Texture.*—Densely covered with short hair (hirtellous).

Inflorescence:

*Start of flowering (50% of plants with open flowers).*—On April 27 (8 weeks old).

*Duration of flowering.*—Continuous flowering from late April throughout the summer.

*Number of inflorescences per plant.*—3–4 in May; About 12–15 in late summer.

*Type and shape of inflorescence.*—Umbel, semi-sphere.

*Number of flowers and buds per inflorescence.*—About 20–25.

*Umbel diameter.*—10.5–11.0 cm in August.

*Umbel depth.*—5.5–6.0 cm.

*Color of peduncle.*—RHS 143C to 144A.

*Length of peduncle.*—12–15 cm.

*Peduncle diameter.*—3 mm.

*Texture.*—Both glandular hair and soft hair.

*Color of pedicel.*—At base most often green, RHS 144B, main portion reddish-brown, RHS 179A or RHS 181A.

*Length of pedicel.*—2.8 cm.

*Diameter of pedicel.*—1.5 mm.

*Texture.*—Covered with very short glandular hair.

Corolla:

*Form.*—Semi-double, nearly flat to weakly cup shaped, nearly round.

*Flower diameter.*—4.7 cm.

*Depth of flower.*—1.0–1.5 cm.

*Number of petals.*—5–8.

*Color upper petals, upper surface.*—RHS N74B, with a large purple-red macule, RHS N57B in the middle and with a white base and purple-pink veins, RHS N74B.

*Color upper petals, lower surface.*—RHS 71D, with fine veins, RHS 67A.

*Length of upper petals.*—2.5–2.8 cm.

*Width of upper petals.*—2.6–2.8 cm.

*Color lower petals, upper surface.*—RHS N74B, with a deep red-purple, medium sized macule, RHS N57A.

*Color lower petals, lower surface.*—RHS 72D.

*Length of lower petals.*—2.4–2.6 cm.

*Width of lower petals.*—2.4–2.8 cm.

*Petal shape.*—Obovate.

*Apex shape.*—Rounded.

*Margin.*—Entire.

*Petal texture.*—Smooth, glabrous.

*Number of petaloids.*—Occassionally 1 or 2, narrower and smaller than petals, often twisted.

*Color of petaloids.*—N74B to N74C.

Bud (just before opening):

*Color.*—N67B.

*Length.*—15–18 mm.

*Width.*—7–8 mm.

*Shape.*—Elliptical.

Calyx:

*Number of sepals.*—5.

*Color of sepals.*—Grass-green, RHS 144A for the outer (abaxial) surface; RHS 144B for the inner surface (adaxial); a little anthocyanin, RHS 179B, possibly at the base of the largest sepal.

*Length of sepals.*—11–12 mm.

*Width of sepals.*—4 mm (largest sepal), 2–3 mm for the other ones.

*Sepal shape.*—Lanceolate.

*Apex shape.*—Acute.

*Margins.*—Entire.

*Texture.*—Covered with glandular hair and a few longer soft hairs.

Reproductive organs:

*Pistil.*—1.

*Length.*—9 mm.

*Style color.*—RHS 67B.

*Style length.*—3–4 mm.

*Stigma color.*—Reddish purple, RHS 67B.

*Number of stamens.*—Up to 7, most often 3–5.

*Length of anthers.*—2–3 mm.

*Anther color.*—RHS 47A.

*Length filaments.*—6–8 mm.

*Color of filaments.*—White, RHS 155D, at base; upper part pink, RHS 68A.

*Pollen amount.*—Moderate (usual amount for the species).

*Color of pollen.*—RHS 28A, yellow orange.

*Fertility/seed set.*—No seed set observed.

Disease/pest resistance: Disease resistance or susceptibility other than typical for the species has not been observed on this hybrid.

What is claimed is:

1. A new and distinct variety of *Pelargonium* plant named 'Fisdelav,' substantially as illustrated and described herein.

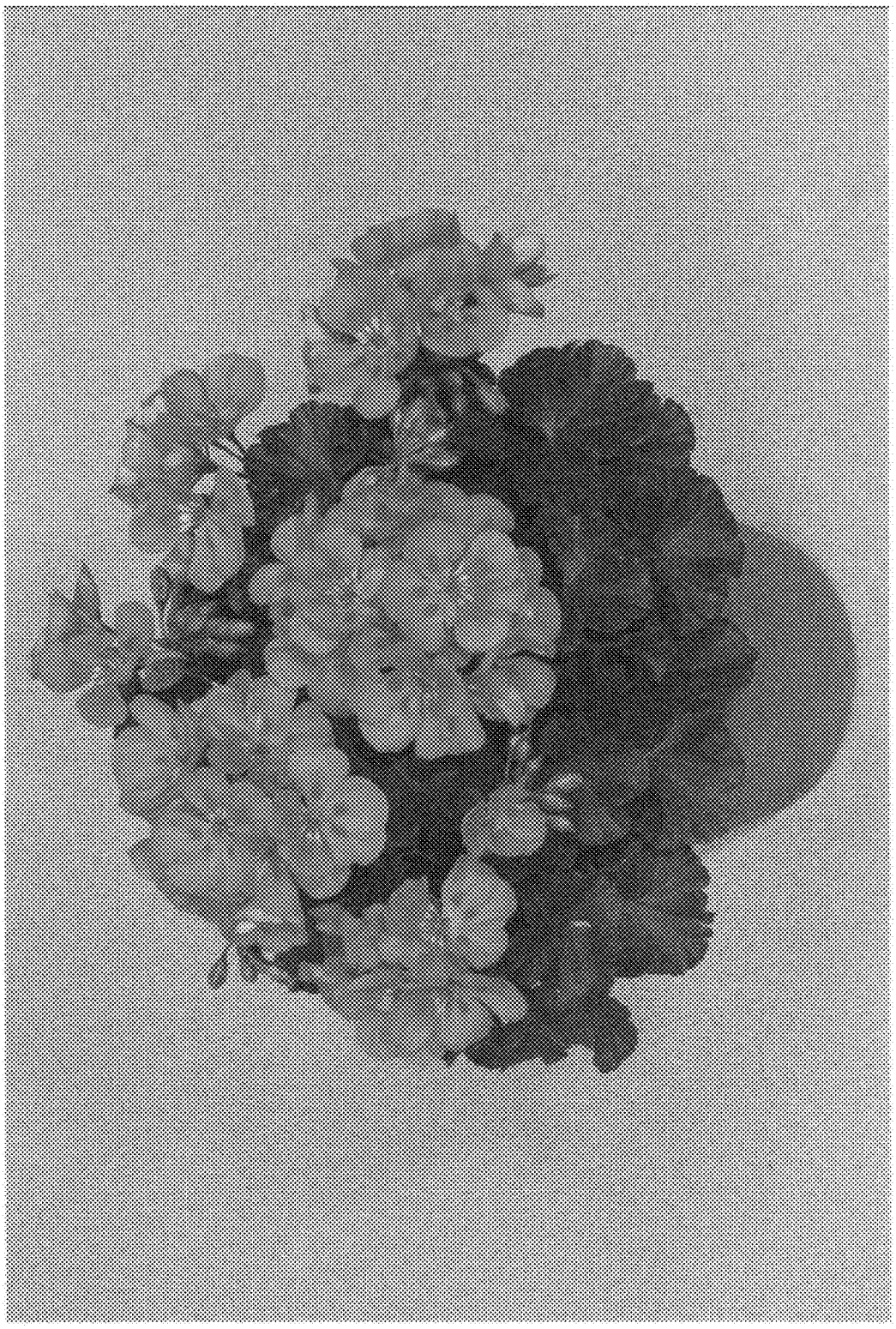

* * * * *